(12) United States Patent
Brodie et al.

(10) Patent No.: US 7,855,362 B1
(45) Date of Patent: Dec. 21, 2010

(54) CONTAMINATION PINNING FOR AUGER ANALYSIS

(75) Inventors: Alan Brodie, Palo Alto, CA (US); Mehran Nasser-Ghodsi, Hamilton, MA (US)

(73) Assignee: KLA-Tencor Technologies Corporation, San Jose, CA (US)

( * ) Notice: Subject to any disclaimer, the term of this patent is extended or adjusted under 35 U.S.C. 154(b) by 506 days.

(21) Appl. No.: 11/924,492

(22) Filed: Oct. 25, 2007

(51) Int. Cl.
*H01J 40/00* (2006.01)

(52) U.S. Cl. ........................ 250/305; 250/306

(58) Field of Classification Search .............. None
See application file for complete search history.

(56) References Cited

U.S. PATENT DOCUMENTS

| | | | | |
|---|---|---|---|---|
| 4,134,014 | A * | 1/1979 | Neave et al. | 250/310 |
| 4,639,301 | A * | 1/1987 | Doherty et al. | 250/251 |
| 6,201,240 | B1 * | 3/2001 | Dotan et al. | 250/310 |
| 6,507,029 | B1 * | 1/2003 | Nishimura et al. | 250/442.11 |
| 6,627,884 | B2 * | 9/2003 | McCord et al. | 850/18 |
| 6,690,010 | B1 * | 2/2004 | Adler | 850/9 |
| 7,560,691 | B1 * | 7/2009 | Gubbens | 250/305 |
| 2004/0183132 | A1 * | 9/2004 | Yamazaki et al. | 257/347 |
| 2008/0042055 | A1 * | 2/2008 | Baykut et al. | 250/287 |
| 2008/0224039 | A1 * | 9/2008 | Nakamura et al. | 250/310 |
| 2009/0321634 | A1 * | 12/2009 | Khursheed | 250/307 |

FOREIGN PATENT DOCUMENTS

WO WO 99/35668 7/1999

OTHER PUBLICATIONS

M Jacka et al., "A Fast, Parallel Acquisition, Electron Energy Analyzer: The Hyperbolic Field Analyzer", *Review of Scientific Instruments* vol. 70, No. 5, May 1999.

* cited by examiner

*Primary Examiner*—Jack I Berman
*Assistant Examiner*—Andrew Smyth
(74) *Attorney, Agent, or Firm*—Joshua D. Isenberg; JDI Patent

(57) ABSTRACT

Electron spectroscopy methods and apparatus are disclosed. A beam of primary electrons is applied to a measurement location on a surface of a sample. A pinning flux of electrons is applied to one or more pinning regions proximate the measurement location. The pinning flux is characterized by a location, size, shape, and electron flux configured such that contaminants preferentially migrate to the pinning region rather than the measurement location. Emissions from the surface resulting from interaction with the primary electrons and the surface of the sample at the measurement location are analyzed.

24 Claims, 5 Drawing Sheets

CONTAMINATION PINNING FOR AUGER ANALYSIS

FIELD OF THE INVENTION

This invention generally relates to Auger electron spectroscopy and more particularly to contamination pinning for Auger electron spectroscopy.

BACKGROUND OF THE INVENTION

Instrumentation for use in spectroscopy of charged particles makes use of electrons or ions which are emitted from a substance after being bombarded or irradiated with primary electrons or ions from a source such as an electron gun. One charged particle spectroscopy technique is known as Auger electron spectroscopy. In this technique, a target sample material is placed in an ultra high vacuum (UHV) environment, typically about $10^{-10}$ Torr to $10^{-9}$ Torr, and upon being bombarded with primary electrons from some source, such as an electron gun, the sample gives off a variety of emissions. Among these are X-rays, secondary electrons, and reflected primary electrons from the source. The emissions include Auger electrons (a particular class of secondary electrons) that are emitted in a manner well known in the art. The energy spectra of these Auger electrons may be analyzed to determine information about chemical species present at the surface of the target. Auger electron spectroscopy typically requires a primary electron energy over voltage that is about 1.5 times an optimum required voltage. This energy is typically sufficiently low that the primary electrons do not damage the sample's surface. Auger electron spectroscopy is useful as a surface analytical technique because the energies of the electrons emitted are typically in the range of 50 eV to 3 KeV, and at this energy they cannot escape from more than a few nanometers deep in the surface (of course, the higher the energy, the thicker the layer from which they can escape).

In the art of Auger electron spectroscopy, electron energy analyzers operate by injecting the diverging electrons into an electric field using a few simply shaped electrodes. Auger electrons injected from the sample into the electric field are deflected by the field such that electrons of a predetermined energy are brought to a focus. By positioning a collector apparatus at this focus, Auger electrons of a predetermined energy may be selected and detected. In some electron energy analyzer designs the voltage impressed across the electrodes may be swept through a range of values and a collector signal may be detected as a function of these applied potentials as the electrons are collected. By plotting or otherwise analyzing the signal (or a derivative thereof) as a function of applied potential, an energy spectrum of the injected electrons may be determined.

Auger electron spectrometers conventionally use a cylindrical mirror analyzer to obtain a secondary electron energy spectrum. A cylindrical mirror analyzer uses electric field between two concentric metal cylinders to select secondary electrons according to energy. Only electrons with the right energy will make it through the field region between the cylinders and strike a detector. A spectrum is obtained by varying the voltage applied between the cylinders and measuring the electron signal as a function of energy.

Auger spectroscopy is often limited by contamination of the sample surface being analyzed. Contaminants, such as hydrocarbons, often collect proximate a location where an electron beam strikes the sample's surface. Such contaminants tend to preferentially migrate or diffuse to the region under electron bombardment. The accumulation of surface contaminants under electron beam scanning can cause a problem for Auger analysis because the Auger electron signal from the contaminants can grow over time to the point that it is larger than the actual target sample. This can limit the useful amount of time for making an Auger measurement.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Figure 1A:
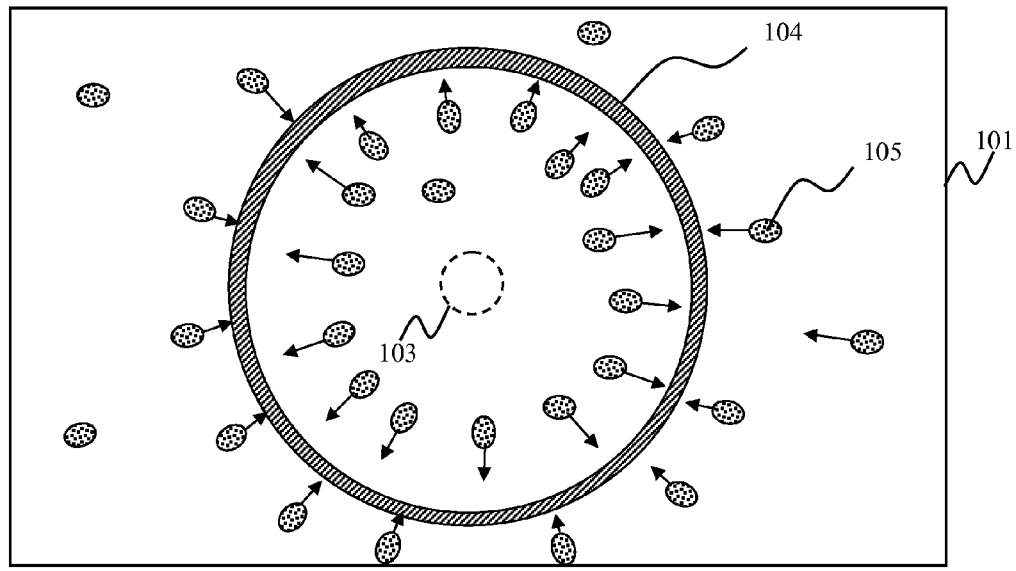
FIGS. 1A-1B are sequential top view diagrams of a sample surface illustrating electron beam pinning of contaminants in conjunction with Auger spectroscopy according to an embodiment of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Embodiments of the present invention take advantage of the fact that contaminants tend to migrate towards places where electrons bombard a surface. Specifically, to keep contaminants away from a measurement location that is bombarded by primary electrons, the contaminants may be pinned by a pinning flux of electrons directed to one or more pinning regions on the surface. If the pinning regions are properly located, sized and shaped and the flux of electrons to the pinning regions is sufficiently large contaminants may be preferably attracted to or "pinned" to the pinning regions. This approach is somewhat counterintuitive in that it solves the contamination problem by taking advantage of the very phenomenon (attraction of the contaminants to target regions subject to electron bombardment) that leads to the contamination problem.

According to embodiments of the present invention a method for electron spectroscopy may involve applying a beam of primary electrons to a measurement location on a surface of a sample and applying a pinning flux of electrons to one or more pinning regions proximate the measurement location. The pinning flux may be characterized by a location, size, shape and electron flux configured such that contaminants preferentially migrate to the pinning region rather than the measurement location. Emissions from the surface resulting from interaction with the primary electrons and the surface of the sample at the measurement location may be analyzed by any suitable technique, such as Auger electron spectroscopy.

Conventionally, it is desirable to capture an Auger spectrum in a time less than or equal to a time to build up about one monolayer of adsorbates, i.e., at about 1 second. A thickness of one monolayer is about 3 Å. The Auger attenuation length usually is about a few tens of Angstroms, e.g., about 10-20 Å. In order to capture useful Auger spectra at the high vacuum, the adsorbates layer may have to be removed since there is noticeable reduction in signal with each monolayer of the adsorbates. Since the carbon peak is often associated with adsorbates it can reasonably be expected that the signal strength of this peak will tend to increase with time, while other peaks associated with the material of the sample can be expected to decrease. Typically, in a high vacuum environment at a background pressure of about $10^{-7}$ Torr to $10^{-6}$ Torr, about one monolayer of the adsorbates, e.g., background gases, including hydrocarbon contaminants, will build up on the surface of the sample in about one to few seconds. Conventional electron analyzers used in Auger spectroscopy often require several seconds to acquire an electron energy spectrum. Consequently, Auger spectroscopy measurements are often performed with the sample in an ultra-high vacuum environment.

In embodiments of the present invention, the pinning flux may delay a buildup of adsorbates (including contaminants such as hydrocarbons) that would otherwise interfere with an Auger electron spectroscopy measurement. Thus, by pinning the contaminants, an Auger spectrum may be obtained at a higher chamber pressure than would otherwise be possible with a conventional Auger system.

Figure 1B:
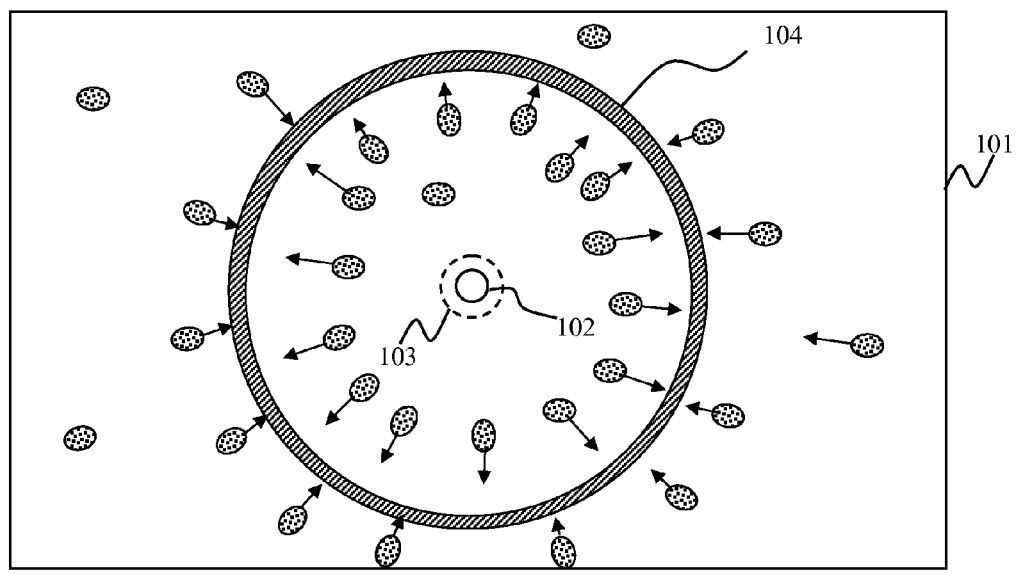

According to one embodiment of the present invention, two separate electron beams may be used to provide the primary electrons and the pinning flux of electrons. For example as shown in FIGS. 1A-1B, a primary electron beam 102 is used to probe a region of interest 103 on the surface of the sample 101 and pinning electron flux 104 is used to pin contaminants 105 and keep the contaminants from the region of interest 103. By way of example, the pinning electron flux 104 may be an annular electron beam that surrounds the region of interest 103. In embodiments of the present invention it is not strictly necessary for the pinning flux to surround the measurement region. However, it is believed that the contaminants will be more effectively pinned if the pinning flux surround the sampled area. In such cases it is also desirable that the pinning flux 104 surround a relatively small area, e.g., large enough to encompass the region of interest 103, but with the pinning flux 104 kept far enough away from the primary electron beam 102 to avoid influencing a detected signal resulting from the primary beam. A roughly circular pinning flux with a diameter of order 10-100 μm may be sufficient depending on the size of the primary electron beam 102 at the surface of the sample 101.

It may be desirable for the pattern of the pinning flux 104 to be larger than the spot where primary electron beam 102 intersects the surface of the sample 101. The actual spot size of the primary beam 102 may be small, e.g., less than 10 nanometers. However, Auger data may be collected by raster scanning the primary electron beam 102 across the surface of the sample 101. The area covered by the resulting raster pattern may be relatively large compared to the actual beam diameter, e.g., as large as a few microns across. In such a case, it may be more desirable for the pinning flux pattern to be larger than the primary beam scanning pattern so that the scanning pattern fits inside the pinning flux 104. Where the primary electron beam is scanned, it may be desirable to have a ratio of pinning pattern size to scan size of about 2:1.

The pinning electron flux 104 may be used to pin the contaminants, as shown in FIG. 1A, before probing the region of interested with the primary beam 102 as shown in FIG. 1B. Electrons in the pinning flux 104 may be accelerated to a different energy than the electrons in the primary electron beam 102. The current and radius of the pinning electron flux 104 may be controlled such that the secondary beam does not affect the primary electron beam 102 but the contaminants are sufficiently pinned, e.g., preferentially migrate, toward locations on the surface of the sample 101 where the pinning flux 104 impinges on the surface. In some embodiments the pinning electron flux 104 may be turned off during periods of Auger measurement of the region of interest 103.

Figure 2A:
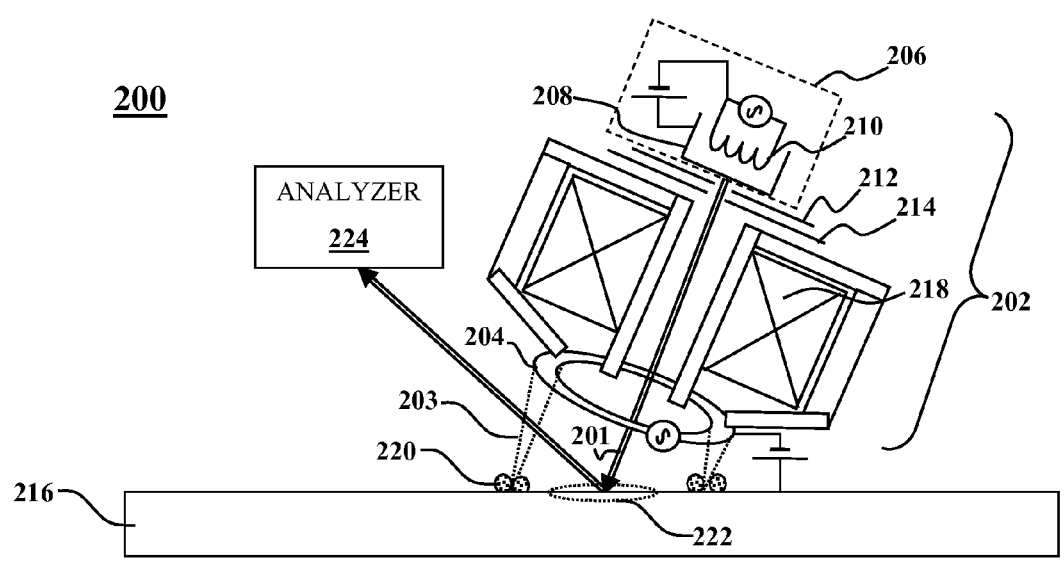
FIG. 2A is a schematic diagram of an electron beam apparatus implementing contamination pinning according to an embodiment of the present invention.

There are several methods to generate the electron flux 104 for pinning the contaminants. FIG. 2A is a schematic diagram apparatus 200 according to an embodiment of the present invention. The apparatus 200 includes a primary electron beam column 202 and a pinning electron flux source 204. The primary electron beam column 202 generates a primary electron beam 201. The primary electron beam column 202 may include an electron source 206. There are numerous electron source configurations that may be used. By way of example, and without loss of generality, the electron source 206 may include a cathode 208 which may be heated by bombardment with electrons from a filament 210. The filament 210 may be heated, e.g., by an electric current and a voltage may be applied between the filament 210 and the cathode 208 to accelerate electrons from the filament 210 to the cathode 208. As the cathode 208 is heated, electrons may be extracted from the cathode 208 e.g., by an accelerating voltage applied between the cathode 208 and an accelerator electrode 212. One or more electron optical lenses 214 (e.g., electrostatic lenses or magnetic lenses) may focus the electrons into the primary beam 201. Numerous variations on the configuration of the electron optical column 202 are possible. For example, in some alternative embodiments, electrons may be extracted directly from the filament 210 and the cathode 208 may be eliminated.

The pinning electron flux source 204 produces a pinning electron flux 203 which may be in the form of an elliptical or circular annular electron beam. The current and the radius of the pinning electron flux 203 may be controlled such that the pinning electron flux 203 sufficiently pins contaminants 220 but does detrimentally affect the primary electron beam 201. The pinning electron flux 203 pins the contaminants 220 and keeps them away from a region of interest 222 on a surface of the sample 216. The primary electron beam 201 may then be used to probe the region of interest 222. Excitation of the region of interest 222 by the primary beam causes electrons to be emitted, and some of the electrons enter electron energy analyzer 224 for an electron spectroscopy and analysis. By way of example, the electron energy analyzer 224 may include a conventional cylindrical mirror analyzer (CMA) as discussed below with respect to FIG. 3A or a hyperbolic field analyzer of the type depicted in FIG. 5 and described in the corresponding discussion thereof.

By way of example, the pinning electron flux source 204 may be in the form of an annular cathode, such as a filament ring, as illustrated in the example depicted in FIG. 2A. The filament ring may be located external to the electron beam column 202 between an end thereof and a sample 216. The filament ring may be concentric with an axis of the primary beam 201 and an axis of the filament ring may be aligned with respect to the axis of the primary beam 201. The filament ring may be heated, e.g., by passing electric current though it. Electrons for the pinning electron flux 203 may be extracted from the ring by applying a voltage between the ring and the sample 216. Magnetic lenses 218 may be used to focus the pinning electron flux 203.

Figure 2B:
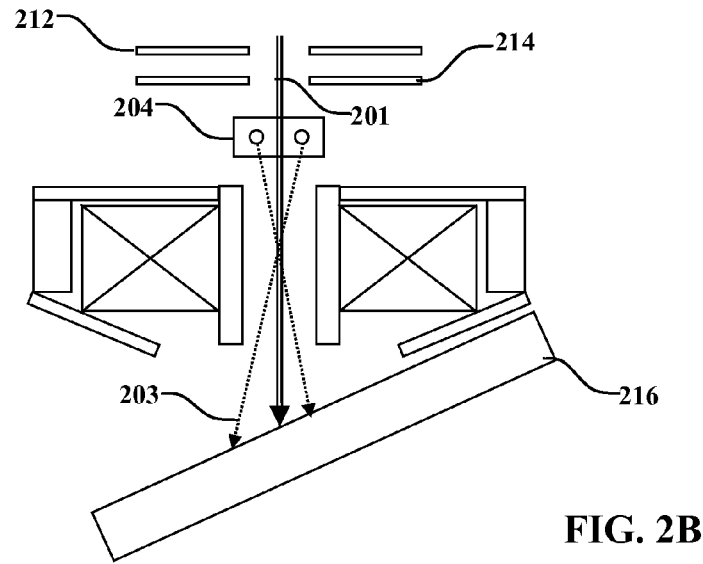
FIG. 2B is a schematic diagram of a portion of an alternative electron beam apparatus implementing contamination pinning according to alternative embodiment of the present invention.

In an alternative embodiment, shown in FIG. 2B the pinning electron flux source 204 may be located within the primary electron beam column 202 between an end thereof and the accelerator electrode 214. As in the embodiment shown in FIG. 2A, the pinning electron flux 204 may include an annular cathode and electrons may be accelerated from the annular cathode toward the sample 216 by an electric field. An electron beam image of the cathode may be formed on the sample 216, e.g., through one or more lenses, such as the magnetic lens 218.

Figure 3A:
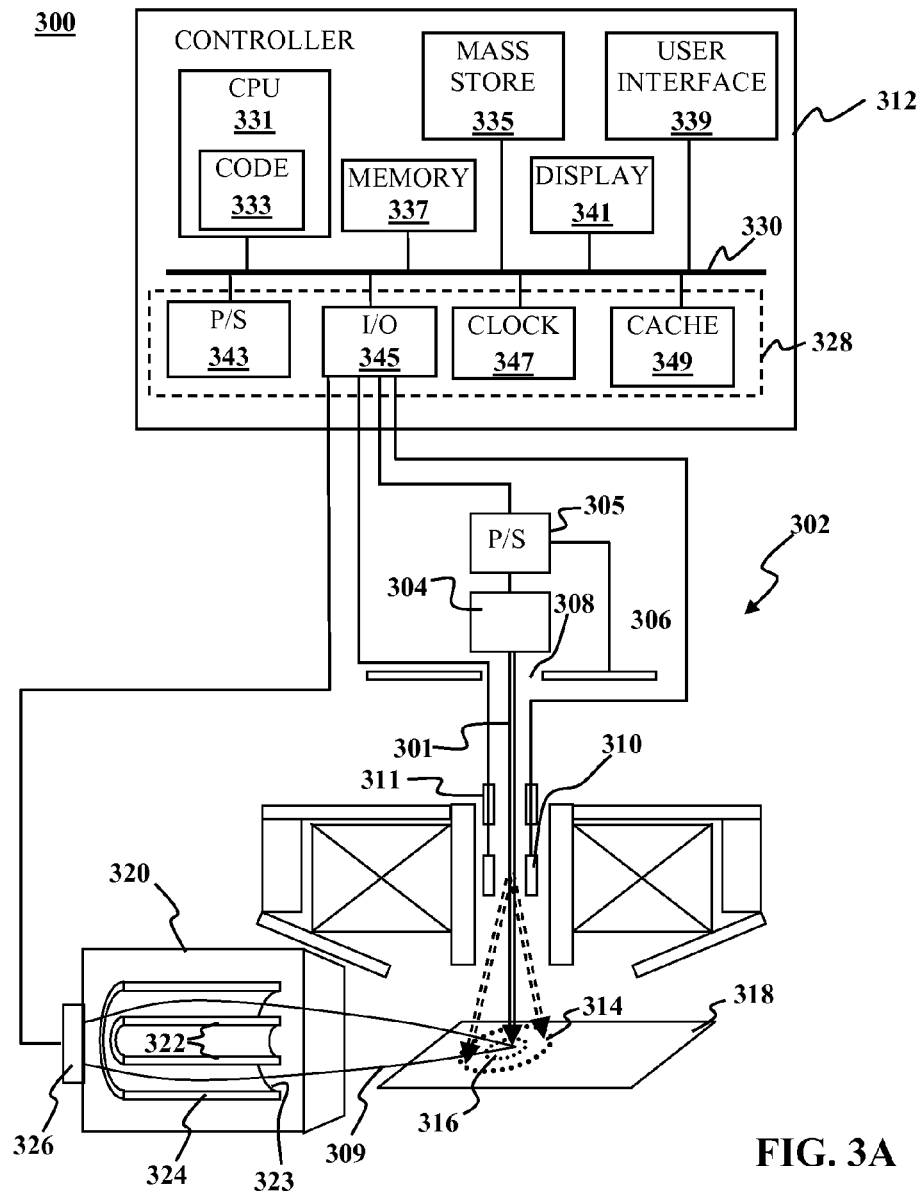
FIG. 3A is a schematic diagram of an electron beam apparatus implementing contaminant pinning according to another alternative embodiment of the invention.
Figure 3B:
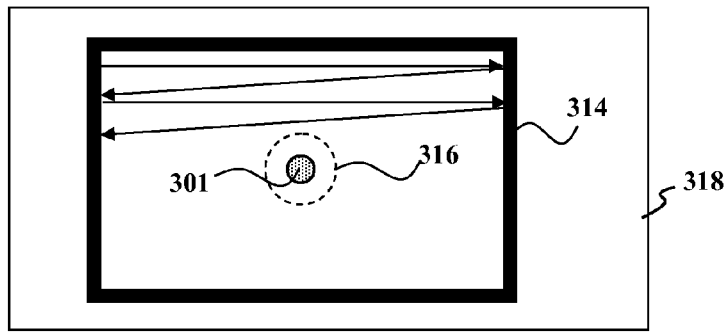
FIG. 3B is a top view of a contaminant pinning electron beam pattern formed with an apparatus of the type shown in FIG. 3A.

Another method for generating an electron flux for pinning the contaminants is described in conjunction with FIG. 3A and FIG. 3B. As shown in FIG. 3A, an electron beam apparatus 300 may include an electron optical column 302 that produces an electron beam 301. The electron optical column may be an electron gun such as that described above with respect to FIG. 2A. The electron optical column 302 may include an electron source 304 and an accelerating electrode 306 having an aperture 308. One or more power supplies 305 coupled to the source 304 and/or accelerating electrode 306 may control the current in the electron beam 301. Electrons may be accelerated through the aperture 308 by an electric field applied between the source 304 and the electrode 306. In addition, the electron optical column 302 may include a beam steering mechanism 310, e.g., a pair of raster plates or electromagnetic deflection coils that facilitate steering of the electron beam 301. The current and position of the electron beam 301 may be controlled through a user-configurable controller 312 coupled to the electrode 306 and beam steering mechanism 310.

The controller 312 may be a self-contained microcontroller. Alternatively, as shown in FIG. 3A, the controller 312 may be a general purpose computer configured to include a central processor unit (CPU) 331, memory 337 (e.g., RAM, DRAM, ROM, and the like) and well-known support circuits 328 such as power supplies 343, input/output (I/O) functions 345, clock 347, cache 349, and the like, coupled to a control system bus 330. The memory 337 may contain instructions that the CPU 331 executes to facilitate the performance of the apparatus 300. The instructions in the memory 337 may be in the form of a program code 333. The code 333 may control, e.g., the focus of the electron beam on the defect, the deflection of the electron beam 301 and the electron beam current and/or energy.

The code 333 may conform to any one of a number of different programming languages such as Assembly, C++, JAVA or a number of other languages. The controller 326 may also include an optional mass storage device, 335, e.g., CD-ROM hard disk and/or removable storage, flash memory, and the like, which may be coupled to the control system bus 330. The controller 312 may optionally include a user interface 339, such as a keyboard, mouse, or light pen, coupled to the CPU 331 to provide for the receipt of inputs from an operator (not shown). The controller 312 may also optionally include a display unit 341 to display images generated by the detector 326 and/or to provide information to the operator in the form of graphical displays and/or alphanumeric characters under control of the processor unit 331. The display unit 341 may be, e.g., a cathode ray tube (CRT) or flat screen monitor.

In this embodiment, the controller 312 may be configured to position and selectively turn on and turn off the electron beam 301 in such a way as to "draw" an electron pinning box 314 is generated a region of interest 316 on the surface of a sample 318, e.g., as shown in FIG. 3B.

The electron beam apparatus 300 may include a high-speed beam blanker to facilitate drawing of the pinning box 314. The single beam 301 from electron column 302 may be raster-scanned and to trace out an edge of the pinning box 314. The single beam may be either off or blanked while tracing the edge of the pinning box 314. The single electron beam 301 may be selectively turned off while the beam steering mechanism is set to steer the beam towards the region of interest 316 for Auger measurement. The pinning box may be drawn prior to positioning the beam 301 in the region of interest so that contaminants have time to migrate to the edge of the pinning box 314 and be pinned or polymerized onto the surface of the wafer. The electron beam 301 may then be positioned for Auger measurement. The controller 312 may be configured to alternate between drawing the pinning box 314 and directing the electron beam 301 to the region of interest 316 for Auger measurement. In this manner an electron optical column that provides a single beam may be configured to provide fluxes of electrons for both contaminant pinning and a primary beam for Auger measurements.

By way of example, the beam blanker may be implemented with the beam steering mechanism 310 in the optical column 302, the power supply 305 and suitable configuration (e.g., hardware or software) of the controller 312 to determine when to blank (i.e., turn off or sufficiently reduce) the current in the electron beam 301. Preferably, the power supply 305 is of a type that can produce a fast rise/fall time for the electron beam 301. The rise/fall time may be regarded as being sufficiently "fast" if the beam blank/unblank occurs within the line retrace time for the electron beam 301. By way of example, and without loss of generality, the line retrace time may be between about 10% and about 20% of the acquisition time.

In some embodiments, a single beam steering mechanism 310 in the optical column 302 may have dual use where they are driven by a fast signal for drawing the pinning box 314 superimposed on a static signal that steers a primary beam spot in the region of interest 316. This allows an existing electron beam column to be used in embodiments of the present invention without having to add or modify any of its components. In alternative embodiments it may be better to use an additional separate dedicated beam steering mechanism 311 coupled to the controller 312 to draw the pinning box 314 since superimposing signals on a single deflection mechanism may add an undesirable degree of noise.

During Auger measurement, secondary electrons from the region of interest 316 may be collected by an electron energy analyzer 320. By way of example, the energy analyzer 320 may be a cylindrical mirror analyzer, as shown in FIG. 3A. This particular type of electron energy utilizes two co-axial conducting cylinders 322, 324 with a voltage applied between the inner cylinder 322 and the outer cylinder 324. Secondary electrons 309 from the sample 318 that enter a gap 323 between the two cylinders 322, 324 will only pass through the gap and reach a detector 326 if the electrons are within a narrow energy range that depends on the voltage between the two cylinders. By scanning the voltage and monitoring the signal from the detector 326 an electron energy spectrum may be obtained.

Figure 4A:
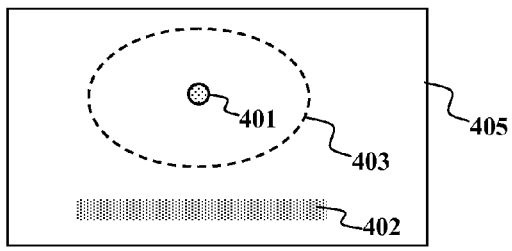
FIGS. 4A-4F are plan view diagrams depicting examples of pinning flux patterns on a sample in accordance with embodiments of the present invention.
Figure 4B:
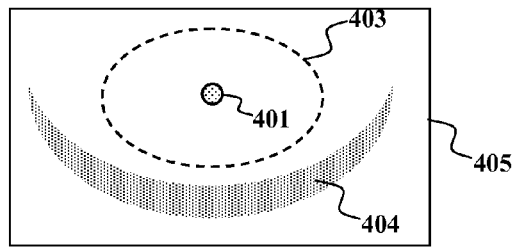
Figure 4C:
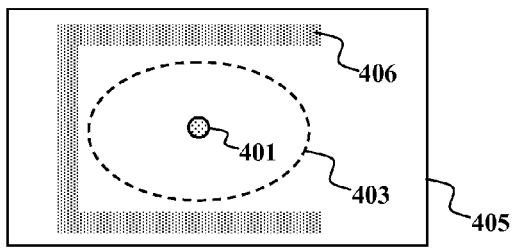
Figure 4D:
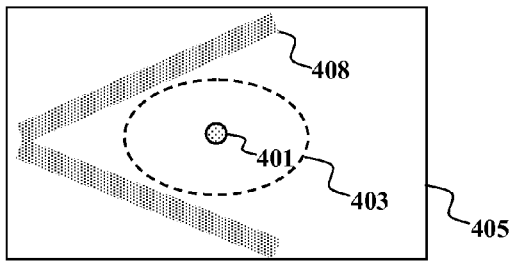
Figure 4E:
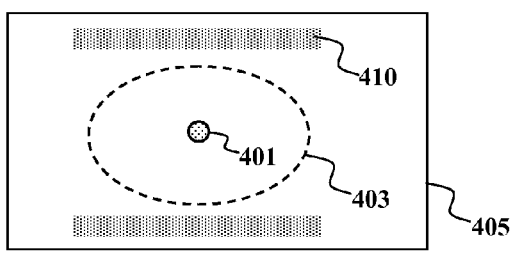
Figure 4F:
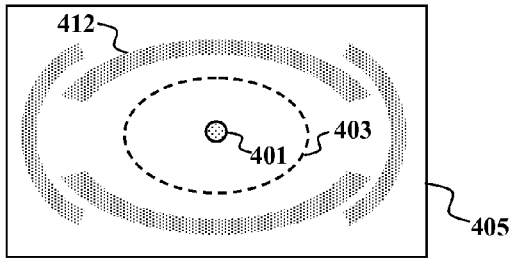

In the examples discussed above, the pinning flux is shown surrounding the region of interest in a circular, elliptical or box-shaped pattern. These are not strict limitations on the invention. It is desirable, however, that the pinning flux bombard the target in a region that is sufficiently large and sufficiently close to the target and with sufficient flux intensity (number of electrons per unit area per unit time in the pinning region) that contaminants are attracted toward the pinning region and away from the region of interest. Any of a number of alternative pinning flux patterns may work. By way of example, and without loss of generality, FIGS. 4A-4F depict a few examples, among others, of suitable pinning flux patterns that are proximate a region of interest 403 on a sample 405. A primary beam of electrons 401 probes the region of interest. The pinning flux patterns include a single straight line pinning flux pattern 402 (FIG. 4A), a single arc pinning flux pattern 404 (FIG. 4B), an open ended box pinning flux pattern 406 (FIG. 4C), a chevron pinning flux pattern 408 (FIG. 4D), a multiple parallel line pinning flux pattern 410 (FIG. 4E) and a multiple arc pinning flux pattern 412 (FIG. 4F). Such patterns may be generated e.g., through appropriate shape of an cathode and or optics used to generate the pinning flux, e.g., as described above with respect to FIGS. 2A-2B or through appropriate raster control used to draw the pinning flux pattern as described above with respect to FIGS. 3A-3B. Those of skill in the art will be able to devise other patterns within the scope of embodiments of the present invention.

Figure 5:
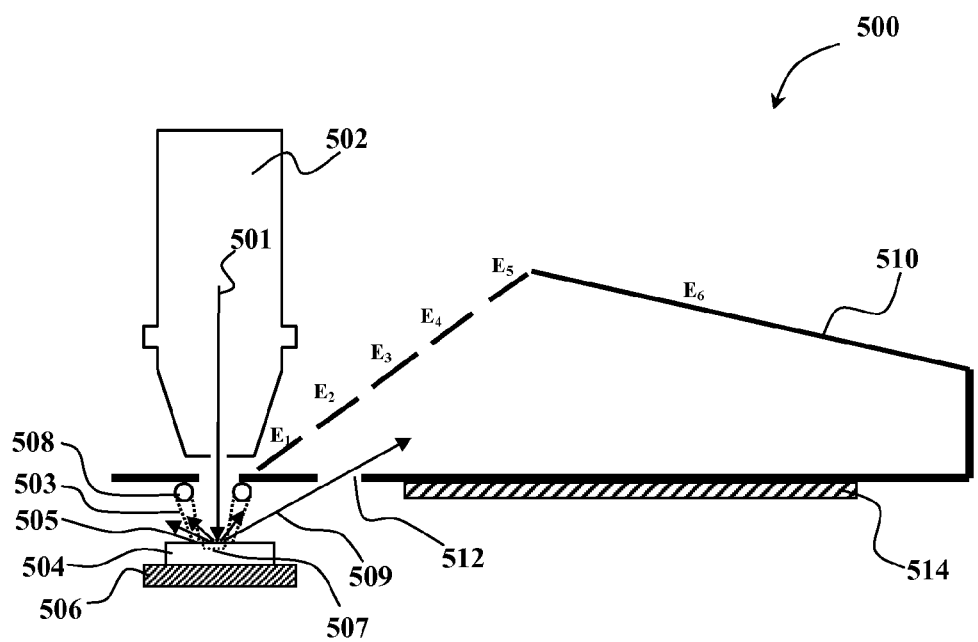
FIG. 5 is a schematic diagram of an Auger electron spectroscopy apparatus utilizing a hyperbolic field analyzer and contaminant pinning according to an embodiment of the present invention.

Embodiments of the present invention are not limited to any particular type of electron energy analyzer. For example, FIG. 5 is a schematic diagram of an electron spectroscopy system 500 that utilizes a pinning electron flux in conjunction with a hyperbolic field analyzer 510. In this example, primary beam 501 of electrons from an electron column 502 bombard the surface of a sample 504 placed on a sample holder 506. A pinning electron source 508 produces a pinning flux 503 of electrons that is directed to a pinning region 505 proximate a region of interest 507 on the surface of the sample 504. Contaminants preferentially migrate toward the pinning region 505 and away from the region of interest 507 as a result of bombardment by the electrons from the pinning flux 503.

Excitation of atoms at or near the surface of the sample 504 by the electrons from the primary beam 501 causes secondary electrons 509 to be emitted from the atoms. Some of the secondary electrons 509 enter the analyzer 510 through an aperture 512, where they are subjected to a substantially hyperbolic field which is approximated with a small number of electrodes, e.g., six electrodes $E_1$ to $E_6$. The electrons are deflected by the substantially hyperbolic field to impinge upon a position sensitive detector 514, which may include a microchannel plate and/or a phosphor screen. Examples of a hyperbolic field analyzer may be found in International Publication No. WO 99/35668 entitled "Charged Particle Analysers" to Prutton et al., filed Jan. 12, 1999, and in "A fast, parallel acquisition, electron energy analyzer: The hyperbolic field analyzer" by M. Jacka et al. in *Review of Scientific Instruments* Vol. 70, No. 5, May 1999, both of which are incorporated herein by reference.

A desirable feature of the electron energy analyzer 510 utilized in this embodiment is an ability to detect electrons over a large range of energy in parallel over an energy range associated with Auger electrons (e.g., about 50 eV to about 2050 eV). In general terms, the substantially hyperbolic field deflects the secondary electrons to impinge upon a detector 514 at different locations depending on secondary electron energy. As discussed above, the detector 514 may include a microchannel plate and a phosphor screen to detect secondary electrons of different energies at different locations. Such detectors may detect electron signals at multiple locations in parallel and produce a separate signal for each location or "channel". Because the signal at each location depends on the energy of electrons that impinge on the detector at that location, the analyzer 510 may obtain a secondary electron energy spectrum in a very short period of time, e.g., on the order of about 1 or 2 seconds. It turns out that this is sufficiently fast that an Auger spectrum could be obtained in a high vacuum environment (about $10^{-6}$ to $10^{-7}$ torr) before more than about 1 to 3 monolayers of adsorbates from background gas would build up on the sample 504. However, some of these adsorbates may be kept from the region of interest 507 by their attraction to the pinning flux 503. This may allow an even longer time for obtaining a secondary electron energy spectrum in a high vacuum environment. Consequently, the analyzer 510 may be used to chemically characterize defects that are too small to image with an SEM or other imaging technique.

Those skilled in the substrate processing arts have long recognized the need for chemical characterization of very small defects. Unfortunately, many of the suggested defect characterization techniques do not provide chemical specific information. For example, transmission Electron Microscopy (TEM) with energy dispersion X-ray (EDX) or energy-loss spectroscopy, has been suggested for characterization of very small defects. Unfortunately, this technique does not provide chemical specific information and further requires a very thin sample for an electron beam to pass through. Scanning tunneling microscopy (STM) in conjunction with I-V curve or scanning near field optical spectroscopy has also been suggested. Although the sample need be thin, the results do not provide chemical specific information.

It is noted that certain pre-existing notions of those in the charged particle spectroscopy and substrate processing arts would weigh against using the analyzer 510 for chemical characterization of defects in a production-scale processing environment. Specifically, those skilled in the charged particle spectroscopy and substrate processing arts associate techniques like Auger spectroscopy with ultra-high vacuum environments, but not high vacuum environments. Thus, those skilled in the substrate processing arts would not expect Auger spectroscopy to work in a production-scale substrate processing environment.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for electron spectroscopy, comprising:
applying a beam of primary electrons to a measurement location on a surface of a sample;
applying a pinning flux of electrons to one or more pinning regions proximate to and outside the measurement location, wherein the pinning flux is characterized by a location, size, shape and electron flux configured such that contaminants preferentially migrate to the pinning region rather than the measurement location, wherein the pinning flux intersects the surface on two or more different sides of the measurement location; and analyzing emissions from the surface resulting from interaction with the primary electrons and the surface of the sample at the measurement location.

2. The method of claim 1 wherein analyzing emissions from the surface includes analyzing secondary electrons emitted as a result of interaction between the primary electrons and the surface of the sample at the measurement location.

3. The method of claim 2 wherein the secondary electrons include Auger electrons.

4. The method of claim 1 wherein the pinning flux intersects the surface in an annular region that surrounds the measurement location, wherein the one or more pinning regions include the annular region.

5. The method of claim 1 wherein the pinning flux intersects the surface in a linear, circular, elliptical, box-shaped, chevron-shaped, or arcuate region that surrounds the measurement location, wherein the one or more pinning regions include the linear, circular, elliptical, box-shaped, chevron-shaped, or arcuate region.

6. The method of claim 1, wherein applying the pinning flux comprises generating electrons with a pinning electron source that is separate from a source of the beam of primary electrons and directing the electrons from the pinning electron source to one or more of the pinning regions.

7. The method of claim 6, wherein the pinning electron source includes an annular electron emitter that surrounds an electron optical axis of a source of the beam of primary electrons.

8. The method of claim 7 wherein directing the electrons from the pinning electron source to the one or more of the pinning regions includes directing the electrons from the annular electron source to an annular region surrounding the measurement location, wherein the one or more pinning regions include the annular region.

9. The method of claim 1 wherein applying the beam of primary electrons and applying the pinning flux of electrons include:

generating a beam of primary electrons; directing the beam of primary electrons toward the surface; and selectively interrupting the beam of primary electrons while scanning the beam of primary electrons across the surface to apply electrons to the measurement location and the one or more pinning regions.

10. The method of claim 9 wherein selectively interrupting the beam of primary electrons while scanning the beam of primary electrons across the surface comprises raster scanning the beam of primary electrons and selectively controlling a current of the beam of primary electrons with a beam blanker.

11. The method of claim 9 wherein applying a beam of primary electrons includes directing the beam of primary electrons toward the measurement location with a first signal applied to a beam steering mechanism and applying the pinning flux includes superimposing a second signal on the first signal applied to the beam steering mechanism to scan the beam of primary electrons across the surface to apply electrons to the one or more pinning regions.

12. The method of claim 9 wherein applying a beam of primary electrons includes directing the beam of primary electrons toward the surface with a first signal applied to a first beam steering mechanism and applying the pinning flux includes applying a second signal to a second beam steering mechanism to scan the beam of primary electrons across the surface to apply electrons to the one or more pinning regions.

13. The method of claim 1 wherein applying the pinning flux and applying the beam of primary electrons includes applying the pinning flux to pin contaminants and then applying the beam of primary electrons after the pinning flux has been applied.

14. An electron spectroscopy apparatus, comprising:

a primary electron source configured to apply a beam of primary electrons to a measurement location on a surface of a sample;

a pinning electron source configured to apply a pinning flux of electrons to one or more pinning regions proximate to and outside the measurement location, wherein the pinning flux is characterized by a location, size, shape and electron flux configured such that contaminants preferentially migrate to the pinning region rather than the measurement location, wherein the pinning flux intersects the surface on two or more different sides of the measurement location; and an analyzer configured to analyze emissions from the surface resulting from interaction with the primary electrons and the surface of the sample at the measurement location.

15. The apparatus of claim 14 wherein analyzer is configured to analyze secondary electrons emitted as a result of interaction between the primary electrons and the surface of the sample at the measurement location.

16. The apparatus of claim 14 wherein the analyzer is configured to analyze Auger electrons emitted as a result of interaction between the primary electrons and the surface of the sample at the measurement location.

17. The apparatus of claim 14 wherein the pinning electron source is configured to apply a pinning flux that intersects the surface in an annular, linear, circular, elliptical, box-shaped, chevron-shaped, or arcuate region that surrounds the measurement location, wherein the one or more pinning regions include the annular, linear, circular, elliptical, box-shaped, chevron-shaped, or arcuate region.

18. The apparatus of claim 14 wherein the pinning electron source is separate from the primary electron source.

19. The apparatus of claim 18, wherein the pinning electron source includes an annular electron emitter that surrounds an electron optical axis of the primary electron source.

20. The apparatus of claim 14 wherein the primary electron source and the pinning electron source comprise a common electron beam source, the apparatus further comprising means for selectively interrupting the common electron beam source while scanning the beam of primary electrons across the surface to apply electrons to the measurement location and the one or more pinning regions.

21. The apparatus of claim 20 wherein the means for selectively interrupting the beam of primary electrons while scanning the beam of primary electrons across the surface includes a beam blanker and means for raster scanning the beam of primary electrons.

22. The apparatus of claim 14 wherein the primary electron source and the pinning electron source comprise an electron beam column having a beam steering mechanism and a controller operable to apply a first signal and second signal superimposed on the first signal to the beam steering mechanism, wherein the first signal is configured to direct the beam of primary electrons toward the measurement location, and wherein the second signal is configured to scan the beam of primary electrons across the surface to apply electrons to the one or more pinning regions to apply the pinning flux.

23. The apparatus of claim 14 wherein the primary electron source and the pinning electron source comprise an electron beam column having a first beam steering mechanism, second beam steering mechanism and a controller operable to apply a first signal to the first beam steering mechanism and a second signal to the second beam steering mechanism, wherein the first signal is configured to direct the beam of primary electrons toward the measurement location, and wherein the second signal is configured to scan the beam of primary electrons across the surface to apply electrons to the one or more pinning regions to apply the pinning flux.

24. An electron spectroscopy apparatus, comprising:
 a primary electron source configured to apply a beam of primary electrons to a measurement location on a surface of a sample;
 a pinning electron source configured to apply a pinning flux of electrons to one or more pinning regions proximate the measurement location, wherein the pinning flux is characterized by a location, size, shape and electron flux configured such that contaminants preferentially migrate to the pinning region rather than the measurement location wherein the primary electron source and the pinning electron source comprise a common electron beam source, the apparatus further comprising means for selectively interrupting the common electron beam source while scanning the beam of primary electrons across the surface to apply electrons to the measurement location and the one or more pinning regions; and an analyzer configured to analyze emissions from the surface resulting from interaction with the primary electrons and the surface of the sample at the measurement location.

* * * * *